United States Patent [19]

Junino et al.

[11] Patent Number: 5,616,809
[45] Date of Patent: Apr. 1, 1997

[54] SULFATED METAAMINOPHENOL COMPOUNDS

[75] Inventors: Alex Junino, Livry-Gargan; Alain Lagrange, Chatou; Alain Genet, Aulnay-sous-Bois, all of France

[73] Assignee: L'Oreal, Paris, France

[21] Appl. No.: 428,619

[22] Filed: Apr. 25, 1995

Related U.S. Application Data

[62] Division of Ser. No. 130,899, Oct. 4, 1993, Pat. No. 5,451,236.

[30] Foreign Application Priority Data

Oct. 2, 1992 [FR] France ................... 92 11712

[51] Int. Cl.$^6$ .................................................. C07C 215/28
[52] U.S. Cl. .................................................. 564/440
[58] Field of Search ............................... 564/440

[56] References Cited

U.S. PATENT DOCUMENTS

| | | | |
|---|---|---|---|
| 3,424,749 | 1/1969 | Pfenninger | 546/197 |
| 3,811,831 | 5/1974 | Bugaut et al. | 8/412 |
| 4,200,466 | 4/1980 | Fujuhara et al. | 430/566 |
| 4,808,752 | 2/1989 | Papenfuhs | 564/414 |
| 5,084,067 | 1/1992 | Junino et al. | 8/421 |
| 5,387,718 | 2/1995 | Köhler et al. | 568/38 |

FOREIGN PATENT DOCUMENTS

| | | |
|---|---|---|
| 331144 | 6/1989 | European Pat. Off. |
| 1061331 | 4/1954 | France. |
| 1321726 | of 1963 | France. |
| 1377649 | of 1964 | France. |
| 2547300 | 12/1984 | France. |
| 4017516 | 12/1991 | Germany. |

OTHER PUBLICATIONS

Chemical Abstracts, Eighth Collective Index, vol. 66–75, 1967–1971, Subjects, p. 30055s.
Chemical Abstracts, Ninth Collective Index, Kvol. 76–85, 1972–1976, Chemical Substances, pp. 6142CS and 6144CS.
Chemical Abstracts, Tenth Collective Index, vol. 86–95, 1977–1981, Chemical Substances, p. 8219CS.

Dallacker et al, "Zur Einfuhrung von Schwefel in Abkommlinge des Brenzcatechinmethylenathers", Annalen der Chemie vol. 689, 1965, pp. 156–162.

Primary Examiner—Brian M. Burn
Attorney, Agent, or Firm—Cushman Darby & Cushman Intellectual Property Group of Pillsbury Madison & Sutro, LLP

[57] ABSTRACT

Sulfated metaaminophenols are disclosed and have the formula

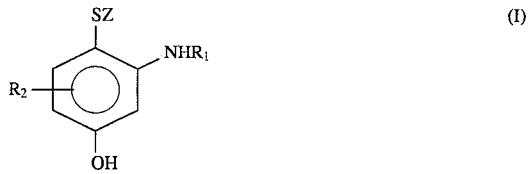

where:

$Z$ is alkyl, aralkyl, monohydroxyalkyl, polyhydroxyalkyl, aryl, aminoalkyl;

$R_1$ is hydrogen, alkyl, monohydroxyalkyl, polyhydroxyalkyl, monocarbamylalkyl, dicarbamylalkyl, aminoalkyl, acylaminoalkyl, carbalkoxyalkyl, carbamyl, or monoalkylcarbamyl;

$R_2$ is hydrogen, alkyl, monohydroxyalkyl, alkoxy;
and their acid salts.

Intermediate products used for their preparation are also disclosed.

These sulfated metaaminophenols are used to dye keratinous fibers.

4 Claims, No Drawings

SULFATED METAAMINOPHENOL COMPOUNDS

This application is a divisional of U.S. Ser. No. 08/130,899, filed Oct. 4, 1993, now U.S. Pat. No. 5,451,236.

BACKGROUND OF THE INVENTION

1. Field of the Invention

The present invention relates to novel sulfated metaaminophenols, the intermediate products necessary for their preparation, their use in dyeing keratinous fibers, in particular as coupling agents in dye compositions, and dyeing methods using these compositions.

2. Description of the Prior Art

It is known to dye keratinous fibers, in particular human hair, using dye compositions containing oxidation dye precursors and coupling agents.

Coupling agents, also known as color modifiers, allow the tints obtained with the oxidation dye precursors to be varied.

In the field of dyeing keratinous fibers, in particular human hair, coupling agents are always being sought which, when associated with oxidation dye precursors, will produce a wide range of hair tints with a play of colors and which have satisfactory resistance to light, washing, bad weather, perspiration and other hair treatments.

The applicant has discovered that novel sulfated metaaminophenols as defined below when used as coupling agents in oxidation dye compositions produce a wide range of tints with a play of colors and which are stable and resistant to light, washing, bad weather, perspiration and other hair treatments.

One object of the present invention is therefore the provision of novel sulfated metaaminophenols.

The invention also provides intermediate products used in the preparation of these sulfated metaaminophenols.

Another object of the invention is the use of these metaaminophenols in dyeing keratinous fibers, in particular human hair.

The invention further provides oxidation dye compositions for use in dyeing keratinous fibers, in particular human hair, containing at least one ortho and/or para type oxidation dye precursor and at least these novel sulfated metaaminophenols as coupling agent.

A still further object of the invention is a method of dyeing keratinous fibers, in particular human hair, using such a composition mixed with an oxidizing agent.

Further objects of the invention will become apparent from the description and examples given hereinafter.

SUMMARY OF THE INVENTION

In one aspect the invention consists in novel sulfated metaaminophenols having general formula:

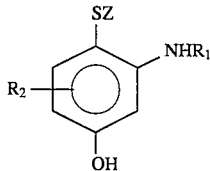
(I)

wherein Z represents a $C_1$–$C_{18}$ alkyl radical, an aralkyl radical wherein the alkyl radical is $C_1$–$C_6$, a $C_1$–$C_6$ mono-hydroxyalkyl or $C_2$–$C_6$ polyhydroxyalkyl radical, an aryl radical, or an aminoalkyl radical having the formula:

wherein n is a whole number from 1 to 6 inclusive;

$R_3$ and $R_4$, which may be identical or different, represent a hydrogen atom or a $C_1$–$C_4$ alkyl radical, a $C_1$–$C_4$ hydroxyalkyl radical or a $C_1$–$C_6$ acyl radical;

$R_1$ represents a hydrogen atom, a $C_1$–$C_6$ alkyl radical, a $C_1$–$C_6$ monohydroxyalkyl radical, a $C_2$–$C_6$ polyhydroxyalkyl radical, a $C_1$–$C_6$ monocarbamylalkyl radical, a $C_1$–$C_6$ dicarbamylalkyl radical, a $C_1$–$C_6$ aminoalkyl radical, an acyl($C_1$–$C_6$)aminoalkyl($C_1$–$C_4$) radical, a carbalkoxy($C_2$–$C_6$)alkyl($C_1$–$C_4$) radical, a $C_1$–$C_6$ carbamyl or monoalkyl radical;

$R_2$ represents a hydrogen atom, a $C_1$–$C_4$ alkyl radical, a $C_1$–$C_4$ monohydroxyalkyl radical, or a $C_1$–$C_4$ alkoxy radical, and their acid salts.

Among the preferred designations for radical Z in sulfated metaaminophenols having general formula (I), the $C_1$–$C_{18}$ alkyl radical may designate methyl, ethyl, propyl, butyl, dodecyl, or hexadecyl; the aralkyl radical may designate benzyl; the aryl radical may designate phenyl; the mono or polyhydroxyalkyl radical may designate —CH$_2$—CH$_2$OH, —CH$_2$—CHOH—CH$_2$—OH, —CH$_2$—CHOH—CH$_3$; the aminoalkyl radical may designate —CH$_2$—CH$_2$—NH$_2$, —CH$_2$—CH$_2$—NHCH$_3$; the acylaminoalkyl radical may designate —CH$_2$—CH$_2$—NH—COCH$_3$; or

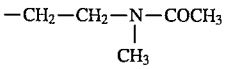

When groups $R_3$ and/or $R_4$ designate the acyl radical, this latter preferably signifies the formyl, acetyl or propionyl radicals;

$R_2$ preferably designates a hydrogen atom or a $C_1$–$C_4$ alkoxy radical.

The corresponding acid salts are preferably selected from hydrochlorides, sulfates and hydrobromides.

Particular sulfated metaaminophenols having formula (I) which may be mentioned are as follows:

2-methoxy 4-methylthio 5-aminophenol 4-methylthio 3-aminophenol or, in accordance with IUPAC nomenclature:

5-amino 2-methoxy 4-methylsulfanylphenol 3-amino 4-methylsulfanylphenol.

Sulfated metaaminophenols having formula (I) and their cosmetically acceptable salts may be prepared in a multi-stage process.

According to a first process, in a first step a halide of 2-nitro 4-OR$_6$-benzene, which may be substituted or not, is reacted in the presence of a base such as potash or potassium carbonate with a thiol having formula (III):

Z'—SH (III)

wherein Z' represents a $C_1$–$C_{18}$ alkyl radical, an aralkyl radical wherein the alkyl radical is $C_1$–$C_6$, a $C_1$–$C_6$ mono-hydroxyalkyl radical, a $C_2$–$C_6$ polyhydroxyalkyl radical, an aryl radical or a group having formula (IV):

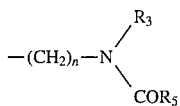

wherein

R$_3$ and n have the meanings indicated above for formula (I);

R$_5$ represents a hydrogen atom or a C$_1$–C$_3$ alkyl radical;

R$_6$ represents a C$_1$–C$_{18}$ alkyl radical, an aralkyl radical, a silyl radical, a pyranyl radical or a hydrogen atom;

in a second step, the nitro substituents on a compound of formula (V):

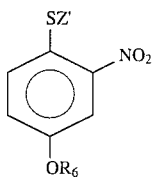

reduced to prepare a compound having formula (VI):

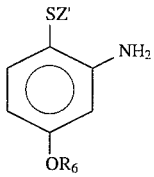

wherein Z' and R$_6$ have the meanings indicated above; if necessary, depending on the sulfated metaaminophenol with formula (I) to be obtained, the following is carried out in a third step:

a) deprotection of the phenolether; or b) monosubstitution of the aromatic amine to produce a compound of formula (I) where R$_1$ is other than H; the —OR$_6$ group may then be deprotected; or c) acid hydrolysis of compound (VI) where Z represents

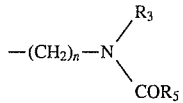

to obtain compound (VII):

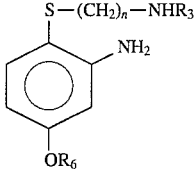

wherein

R$_3$, R$_6$ and n have the meanings given above, although R$_3$ may not designate the C$_1$–C$_6$ acyl radical; the nuclear amine may then be monosubstituted and the —OR$_6$ group deprotected; or d) first substituting the extranuclear amine in compound (VI) where Z' represents the group. (IV) to produce compound (VIII):

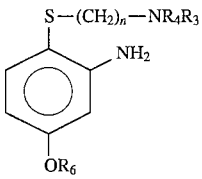

wherein R$_3$, R$_4$, R$_6$, and g have the meanings given above; the nuclear amine may then be monosubstituted and the —OR$_6$ group deprotected.

These steps may be followed by substitution in the benzene ring of a R$_2$ group having the meaning given above although it may not designate a hydrogen atom.

In the first step of a second process a substituted compound having formula (IX):

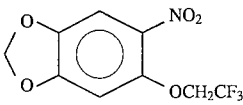

is reacted with a thiol having formula:

Z'—SM (X)

where M is an alkaline radical and Z' has the meaning given above to obtain a compound with formula (XI):

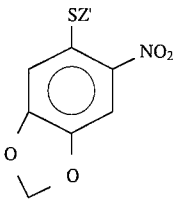

The dioxolane ring of the compound of formula (XI) is opened using an alcoholate in a third stage to prepare a compound having formula (XII):

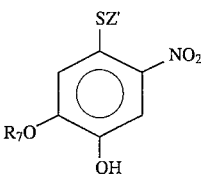

R$_7$ represents a linear or branched C$_1$–C$_4$ alkyl group.

Reduction of the nitro groups of compounds (V) or (XII) is preferably carried out using iron in an acetic medium or by cyclohexene in the presence of a palladium-carbon catalyst or using powdered zinc in the presence of ammonium chloride and ethanol or by any other conventional reduction technique.

Substitution of the aromatic or extranuclear amine may be effected by reaction with ethyl bromide, glycol bromohydrin, ethylchloroformiate, β-chloracetamide or acetic anhydride, for example.

The invention also relates to novel intermediate compounds having formula (V), (XI) or (XII) as defined above, which can be used in the synthesis of metaaminophenols having formula (I).

In another aspect the invention consists in the use of at least one sulfated metaaminophenol having formula (I) as defined above in dyeing keratinous fibers, in particular human hair.

Compounds having formula (I) are applied to the keratinous fibers, in particular human hair, in a dye composition which constitutes the invention in a further aspect.

Compositions in accordance with the invention contain at least one sulfated metaaminophenol as defined above in an appropriate dye medium. Preferred compositions contain at least one sulfated metaaminophenol as defined above as a coupling agent, in association with at least one ortho and/or para type oxidation dye precursor.

The ortho and/or para type dye precursors used in the compositions are compounds which are not themselves dyes but form a dye by an oxidative condensation process either with themselves or in the presence of a coupling agent or modifier.

These ortho or para type oxidation dye precursors are benzene derivatives or heterocyclic compounds comprising two functional amino groups or a hydroxy and an amino group in the ortho or para position relative to each other.

Ortho or para type oxidation dye precursors may be selected from paraphenylenediamines, paraaminophenols, para heterocyclic derivatives of pyridine, pyrimidine or pyrazole such as 2,5-diaminopyridine, 2-hydroxy 5-aminopyridine, 2,4,5,6-tetraaminopyrimidine, 4,5-diamino 1-methylpyrazole, 2-dimethylamino 4,5,6-triaminopyrimidine, orthoaminophenols and so-called double bases.

Regarding the paraphenylenediamines, compounds having formula (XIII) may in particular be cited:

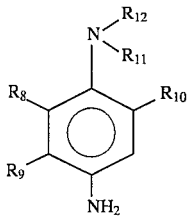

(XIII)

wherein:

$R_8$, $R_9$, $R_{10}$, which may be identical or different, represent a hydrogen or halogen atom, an alkyl radical, an alkoxy radical, or a carboxy, sulfo or hydroxy ($C_1$–$C_4$) alkyl radical;

$R_{11}$ and $R_{12}$, which may be identical or different, represent a hydrogen atom, alkyl, hydroxyalkyl, alkoxyalkyl, carbamylalkyl, mesylaminoalkyl, acetylaminoalkyl, ureidoalkyl, carbalkoxyaminoalkyl, sulfoalkyl, piperidinoalkyl, morpholinoalkyl or phenyl which may be para substituted by an amino group; or $R_{11}$ and $R_{12}$ together with the nitrogen atom to which they are bonded form a piperidino or morpholino heterocycle, providing that $R_8$ or $R_{10}$ represent a hydrogen atom when $R_{11}$ and $R_{12}$ do not represent a hydrogen atom, including the salts of these compounds. The alkyl or alkoxy radicals preferably contain one to four carbon atoms and in particular designate methyl, ethyl, propyl, methoxy and ethoxy radicals.

Particular compounds with formula (XIII) are as follows:
paraphenylenediamine,
p-toluylenediamine,
methoxyparaphenylenediamine,
chloroparaphenylenediamine,
2,3-dimethylparaphenylenediamine,
2,6-dimethylparaphenylenediamine,
2,6-diethylparaphenylenediamine,
2,5-dimethylparaphenylene-diamine,
2-methyl 5-methoxyparaphenylenediamine,
2,6-dimethyl 5-methoxyparaphenylenediamine,
N,N-dimethylparaphenylenediamine,
N,N-diethylparaphenylenediamine,
N,N-dipropylparaphenylene-diamine,
3-methyl 4-amino N,N-diethylaniline,
N,N-di-(β-hydroxyethyl)paraphenylenediamine,
3-methyl 4-amino N,N-di-(β-hydroxyethyl)aniline,
3-chloro 4-amino N,N-di-(β-hydroxyethyl)aniline,
4-amino N,N-(ethyl, carbamylmethyl)aniline,
3-methyl 4-amino N,N-(ethyl, carbamylmethyl)aniline,
4-amino N,N-(ethyl, β-piperidinoethyl)aniline,
3-methyl 4-amino N,N-(ethyl, β-piperidinoethyl)aniline,
4-amino N,N-(ethyl, β-morpholinoethyl)aniline,
3-methyl 4-amino N,N-(ethyl, β-morpholinoethyl)aniline,
4-amino N,N-(ethyl, β-acetylaminoethyl)aniline,
4-amino N-(β-methoxyethyl)aniline,
3-methyl 4-amino N,N-(ethyl, β-acetylaminoethyl)aniline,
4-amino N,N-(ethyl, β-mesylaminoethyl)aniline,
3-methyl 4-amino N,N-(ethyl, β-mesylaminoethyl)aniline,
4-amino N,N-(ethyl, β-sulfoethyl)aniline,
3-methyl 4-amino N,N-(ethyl, β-sulfoethyl)aniline,
N-[(4'-amino)phenyl]-morpholine,
N-[(4'-amino)phenyl]piperidine,
2-hydroxyethylparaphenylenediamine,
fluoroparaphenylenediamine,
carboxyparaphenylenediamine,
sulfoparaphenylenediamine,
2-isopropylparaphenylenediamine,
2-n-propylparaphenylenediamine,
hydroxy-2-n-propylparaphenylenediamine,
2-hydroxymethylparaphenylenediamine,
N,N-dimethyl 3-methylparaphenylenediamine,
N,N-(ethyl,β-hydroxyethyl)paraphenylenediamine,
N-(dihydroxypropyl)-paraphenylenediamine,
N-4'-aminophenylparaphenylenediamine,
N-phenylparaphenylenediamine.

These paraphenylenediamines may be used in the dye composition either in the form of the free base or as a salt such as the hydrochloride, hydrobromide or sulfate.

Particular p-aminophenols which may be mentioned are as follows:
p-aminophenol,
2-methyl 4-aminophenol,
3-methyl 4-aminophenol,
2-chloro 4-aminophenol,
3-chloro 4-aminophenol,
2,6-dimethyl 4-aminophenol,
3,5-dimethyl 4-aminophenol,
2,3-dimethyl 4-aminophenol,
2,5-dimethyl 4-aminophenol,
2-hydroxymethyl 4-aminophenol,
2-(β-hydroxyethyl) 4-aminophenol,
2-methoxy 4-aminophenol,
3-methoxy 4-aminophenol,
3-(β-hydroxyethoxy) 4-aminophenol,
2-methoxymethyl 4-aminophenol,
2-aminomethyl 4-aminophenol,
2-β-hydroxyethylaminomethyl 4-aminophenol,
2-ethoxymethyl 4-aminophenol, 2-(β-hydroxyethoxy)methyl 4-aminophenol.

The so-called double bases are bis-phenylalkylenediamines corresponding to the formula:

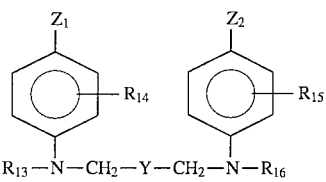 (XIV)

wherein:

$Z_1$ and $Z_2$, which may be identical or different, represent hydroxyl groups or $NHR_{17}$ groups where $R_{17}$ designates a hydrogen atom or a low alkyl radical;

$R_{14}$ and $R_{15}$, which may be identical or different, represent hydrogen atoms, halogen atoms or alkyl radicals;

$R_{13}$ and $R_{16}$, which may be identical or different, represent a hydrogen atom, an alkyl or hydroxyalkyl radical or an aminoalkyl radical wherein the amine moiety may be substituted; Y represents a radical selected from the following:

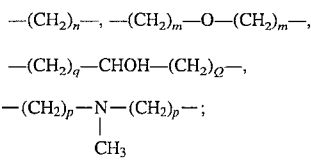

where n is a whole number between 0 and 8 and m q and p are whole numbers between 0 and 4. This base may also be in the form of addition salts with acids.

The alkyl or alkoxy radicals indicated above preferably designate a group having one to four carbon atoms, in particular methyl, ethyl, propyl, methoxy and ethoxy.

Particular compounds having formula (IV) which may be mentioned are as follows:

N,N'-bis-(β-hydroxyethyl) N,N'-bis-(4'-aminophenyl) 1,3-diamino 2-propanel,

N,N'-bis-(β-hydroxyethyl) N,N'-bis-(4'-aminophenyl)ethylenediamine,

N,N'-bis-(4-aminophenyl)tetramethylenediamine,

N,N'-bis-(β-hydroxyethyl) N,N'-bis-(4-aminophenyl)tetramethylenediamine,

N,N'-bis-(4-methylaminophenyl)tetramethylenediamine, and

N,N'-bis-(ethyl) N,N'-bis-(4'-amino 3'-methylphenyl) ethylenediamine.

The ortho type oxidation dye precursors are selected from orthoaminophenols such as:

1-amino-2-hydroxybenzene, 6-methyl 1-hydroxy 2-aminobenzene, 4-methyl 1-amino 2-hydroxybenzene, and orthophenylenediamines.

The dye compositions described above used to dye keratinous fibers may also contain, as well as the coupling agent having formula (I) as defined above, other known coupling agents such as:

metadiphenols, metaaminophenols other than those having formula (I), metaphenylenediamines, metaacylaminophenols, metaureidophenols, metacarbalkoxyaminophenols, α-napthol, indole derivatives, coupling agents containing an active methylene group such as β-ketones, and pyrazolones.

The following coupling agents may in particular be mentioned:

2,4-dihydroxyphenoxyethanol, 2,4-dihydroxyanisole, metaaminophenol, resorcinol monomethylether, resorcinol, 2-methyl resorcinol, 2-methyl 5-aminophenol 2-methyl 5-N-(β-hydroxyethyl) aminophenol, 2-methyl 5-N-(β-mesylaminoethyl) aminophenol, 2,6-dimethyl 3-aminophenol, 6-hydroxybenzomorpholine, 2,4-diaminoanisole, 2,4-diaminophenoxyethanol, 6-aminobenzomorpholine,

[2-N-(β-hydroxyethyl) amino 4-amino]-phenoxyethanol, 2-amino 4-N-(β-hydroxyethyl) aminoanisole, (2,4-diamino)phenyl-β-γ-dihydroxypropylether, 2,4-diaminophenoxyethylamine, 1,3-dimethoxy 2,4-diaminobenzene, 1,3,5-trimethoxy 2,4-diaminobenzene, 1-amino 3,4-methylenedioxybenzene, 1-hydroxy 3,4-methylenedioxybenzene, 2-chloro 6-methyl 3-aminophenol, 2-methyl 3-aminophenol, 2-chlororesorcinol, 6-methoxy 3-hydroxyethylaminoaniline, 1-ethoxy 2-bis(β-hydroxyethyl)amino 4-aminobenzene, 3-diethylaminophenol, 1,3-dihydroxy 2-methylbenzene, 1-hydroxy 2,4-dichloro 3-aminobenzene, 4,6-di(hydroxyethoxy) 1,3-diaminobenzene, 4-methyl 6-ethoxy 1,3-diaminobenzene, 4-chloro 6-methyl 3-aminophenol, 6-chloro 3-trifluoroethylaminophenol, and salts thereof.

Direct dyes may be added to such compositions, as is known in the art, in particular to shade or enrich the lustre of the colors attained by the oxidation dye precursors. Examples of direct dyes are azo and anthraquinone dyes or nitro compounds of the benzene series.

The total amount of para and/or ortho type oxidation dye precursors plus the coupling agents used in dye compositions in accordance with the invention preferably comes to 0.3 to 7% by weight with respect to the weight of said composition. The concentration of sulfated metaaminophenols of formula (I) may vary between 0.05 and 3.5% by weight with respect to the composition weight.

A preferred embodiment of a dye composition also contains a known anionic, cationic, non-ionic or amphoteric surfactant or mixture thereof.

These surfactants are present in proportions of between 0.5 and 55% by weight, preferably between 2 and 50% by weight with respect to the total composition weight.

These compositions may also contain organic solvents to solubilize components which are insufficiently soluble in water. Particular solvents which may be mentioned are:

$C_1$–$C_4$ low alkanols, such as ethanol and isopropanol; glycerol;

glycols or glycol ethers such as 2-butoxyethanol, ethyleneglycol, propyleneglycol, diethyleneglycol monoethylether and monomethylether; aromatic alcohols such as benzyl alcohol or phenoxyethanol; analogous products, and mixtures thereof.

The solvents are preferably present in proportions of between 1 and 40% by weight, particularly between 5 and 30% by weight with respect to the total composition weight.

Thickening agents may be added to the compositions, for example sodium alginate, gum arabic, acrylic acid polymers which may be reticulated, cellulose derivatives, or heterobiopolysaccharides such as xanthane gum. Mineral thickening agents such as bentonite may also be used.

The thickening agents are preferably present in proportions of between 0.1 and 5%, in particular between 0.2 and 3% by weight with respect to the total composition weight.

Antioxidants which may be present in the compositions are preferably selected from sodium sulfite, thioglycolic acid, sodium bisulfite, dehydroascorbic acid, hydroquinone and homogentisic acid. These antioxidants are present in the composition in proportions of between 0.05 and 1.5% by weight with respect to the total composition weight.

These compositions may further contain other cosmetically acceptable additives such as penetrating agents, sequestrum producing agents, perfume, buffers, dispersing agents, processing agents, packaging agents, film forming agents, preservatives, opacifying agents, etc.

A composition according to the invention contains a sulfated metaaminophenol having formula (I) and an ortho and/or para type oxidation dye precursor. The composition pH lies between 3 and 10.5. It is adjusted to the desired value using known alkalizing agents such as ammonia, alkaline carbonates, alkanolamines such as mono-, di- and triethanolamines and their derivatives, or sodium or potassium hydroxide; or standard acidifying agents, for example mineral or organic acids such as hydrochloric, tartaric, citric or phosphoric acid.

Compositions to be applied to hair may take a number of different forms, for example liquid, cream, gel or any other form appropriate to dyeing keratinous fibers, in particular human hair. The compositions may be packaged in aerosol cans with a propellant to produce a foam.

Compounds of formula (I) are used in a method comprising applying a compound having formula (I) and oxidation dye precursors in the presence of an oxidizing agent to the keratinous fibers, in particular human hair.

These compounds may be applied simultaneously in a dye composition as defined above or successively in a multistage method.

Dye compositions in accordance with the invention containing a para and/or ortho type oxidation dye precursor and a coupling agent of formula (I) are used in a method using an oxidizing agent as developer.

The oxidizing agent is preferably selected from hydrogen peroxide, alkali metal bromates and persalts such as perborates and persulfates. Hydrogen peroxide is particularly preferred.

Using this method, when required for use the dye composition described above is mixed with an oxidizing solution in sufficient quantity to develop the color. The mixture thus obtained is then applied to the keratinous fibers, in particular human hair.

The pH of the composition applied to the hair preferably varies between 2 and 13. It is adjusted to the desired value using known alkalizing agents or acidifying agents as described above. The oxidizing solution contains, as the oxidizing agent, hydrogen peroxide, urea peroxide, peroxy salts such as ammonium persulfate, or alkali metal bromides. A 20 volume solution of hydrogen peroxide is preferably used.

The mixture obtained is applied to the hair and left for 10 to 40, preferably 15 to 30 minutes. The hair is then rinsed, shampooed, rinsed again and dried.

The coupling agent of formula (I) defined above may also be used in a multistage method, one step of which consisting in applying the ortho and/or para oxidation dye precursor(s), or a mixture of these, and another consisting in applying a dye composition containing the coupling agent of formula (I). The oxidizing agent may be introduced into the composition just before application in the second step or it may be applied directly to the keratinous fibers in a third step. Application, pH, washing and drying conditions are as indicated above.

DETAILED DESCRIPTION OF THE INVENTION

The following examples are intended to illustrate but not to limit the scope of the invention.

EXAMPLE 1

Preparation of 4-methylthio-3-aminophenol hydrochloride, denominated in accordance with IUPAC nomenclature as 3-amino-4-methlsulfanylphenol hydrochloride.

Step 1: Synthesis of [2-nitro-4-(benzyloxy)phenylmethylsulfane.

65.9 g (0.25 mole) of 1-chloro-2-nitro-4-(benzyloxy)benzene was added portionwise to a suspension of sodium thiomethylate (0.35 mole) in 100 ml dimethoxyethane at room temperature.

The reaction was exothermic. The mixture was cooled to maintain the temperature between 25° and 30° C. The reaction mixture was poured into a litre of iced water. The crystalline precipitate was dried then taken up in water.

After recrystallization from 96° ethanol then isopropyl acetate, 34.4 g of orange crystals were obtained which melted at 78° C. Elemental analysis calculated for $C_{14}H_{13}NO_3S$ was as follows:

| % | C | H | N | O | S |
| --- | --- | --- | --- | --- | --- |
| Calculated | 61.07 | 4.76 | 5.09 | 17.43 | 11.65 |
| Found | 61.30 | 4.81 | 4.90 | 17.34 | 11.57 |

Step 2: Synthesis of 2-methylsulfanyl-5-(benzyloxy)phenylamine.

A mixture of 2.2 g ammonium chloride, 15 ml water, 140 ml 96° alcohol and 70 g finely powdered zinc was heated under reflux. The [2-nitro-4-(benzyloxy)phenyl]methylsulfane obtained from step 1 was added portionwise (33.8 g, 0.123 mole) so as to maintain the reflux without heating.

The reduction was exothermic. Following addition, heating under reflux was continued for 15 minutes.

The decolorized reaction medium was boil filtered. On cooling the filtrate, pale yellow crystals precipitated which were dried (28.2 g).

Following recrystallization from cyclohexane, this compound melted at 64° C. Elemental analysis calculated for $C_{14}H_{15}NOS$ was as follows:

| % | C | H | N | O | S |
|---|---|---|---|---|---|
| Calculated | 68.54 | 6.16 | 5.71 | 6.52 | 13.07 |
| Found | 68.40 | 6.11 | 5.61 | 6.72 | 13.11 |

Step 3:

The 28.2 g (0.115 mole) of 2-methylsulfanyl-5-(benzyloxy)phenylamine obtained from step 2 was heated at 90°–95° C. in a mixture of 50 ml of 36% hydrochloric acid and 5 ml water for one hour.

The suspension was then cooled in an ice bath.

After vacuum drying over potash and recrystallization from absolute ethanol, 8.3 g of white crystals of 3-amino-4-methylsulfanylphenol hydrochloride were obtained which melted with decomposition at 210°–214° C. Elemental analysis calculated for $C_7H_{10}ClNOS$ was as follows:

| % | C | H | N | S | Cl |
|---|---|---|---|---|---|
| Calculated | 43.86 | 5.26 | 7.31 | 16.73 | 18.50 |
| Found | 43.36 | 5.42 | 7.08 | 16.46 | 18.26 |

EXAMPLE 2

Preparation of 2-methoxy-4-methylthio-5-aminophenol hydrochloride, denominated in accordance with IUPAC nomenclature as 5-amino-2-methoxy-4-methylsulfanylphenol hydrochloride.

Step 1: Synthesis of 2-methoxy-4-methylsulfanyl-5-nitrophenol.

A suspension of 50.5 g (0.237 mole) methyl-(6-nitrobenzo[1,3]dioxol-5-yl)-sulfane in 230 ml methanol was heated under reflux.

105 ml of a solution of 30% sodium methylate in methanol was added dropwise.

The heating under reflux was continued for 4 hours.

The mixture was cooled in an ice bath and the sodium phenate of the expected compound was dried. Following dissolution of the phenate in 2 liters of water and acidification with a concentrated hydrochloric acid solution, the crystalline precipitate was dried, taken up again in water and dried again.

After recrystallization from isopropanol, 44.5 g of yellow crystals were obtained which melted at 158° C. Elemental analysis calculated for $C_8H_9NO_4S$ was as follows:

| % | C | H | N | O | S |
|---|---|---|---|---|---|
| Calculated | 44.65 | 4.21 | 6.51 | 29.73 | 14.90 |
| Found | 44.62 | 4.21 | 6.42 | 29.95 | 14.72 |

Step 2: Reduction.

The compound obtained from step 1 (18.8 g–0.0873 mole) was reduced using the method described for example 1 step 3, the reaction mixture being boil filtered into hydrochloric acid in absolute ethanol.

9.6 g of white crystals of 5-amino-2-methoxy-4-methylsulfanylphenol hydrochloride were obtained which melted with decomposition at 235°–240° C. Elemental analysis calculated for $C_8H_{12}ClNO_2S$ was as follows:

| % | C | H | N | O | S | Cl |
|---|---|---|---|---|---|---|
| Calculated | 43.34 | 5.46 | 6.32 | 14.43 | 14.46 | 15.99 |
| Found | 43.55 | 5.52 | 6.20 | 14.67 | 14.22 | 15.80 |

EXAMPLES OF COMPOSITIONS

EXAMPLE 1

| | |
|---|---|
| 4-methylthio 3-aminophenol hydrochloride | 0.383 g |
| Paraphenylenediamine | 0.216 g |
| Octyldodecanol sold under the trade name EUTANOL D by HENKEL | 8 g |
| Oleic alcohol | 20 g |
| Monoethanolamine laurylethersulfate sold under the trade name SIPON LM 35 by HENKEL | 3 g |
| Ethyl alcohol | 10 g |
| Benzyl alcohol | 10 g |
| Cetylstearyl alcohol oxyethylenated to 33 moles ethylene oxide sold under the trade name SIMULSOL GS by SEPPIC | 2.4 g |
| Ethylenediamine tetracetic acid | 0.2 g |
| Cationic polymer solution containing the following: | 3.7 g |

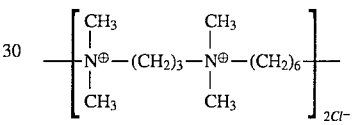

| | |
|---|---|
| to 60% M.A. | |
| monoethanolamine | 7.5 g |
| Diethanolamide of linoleic acid sold under the trade name COMPERLAN F by HENKEL | 8 g |
| Ammonia solution, 20% $NH_3$ | 10.2 g |
| Sodium metabisulfite, 35% aqueous solution | 1.3 g |
| Hydroquinone | 0.15 g |
| 1-phenyl 3-methyl 5-pyrazolone | 0.2 g |
| Demineralized water q.s.p. | 100 g |

This composition was mixed just before use with an equal weight of 20 vol hydrogen peroxide with a pH of 3. The pH of the mixture was equal to 9.5. The mixture was applied to permed gray hair and left for 30 minutes at room temperature. The hair was then rinsed, shampooed and dried. It was dyed a dark beige blond.

EXAMPLE 2

| | |
|---|---|
| 2-methoxy 4-methylthio 5-aminophenol hydrochloride | 0.665 g |
| 2,6-dimethyl paraphenylenediamine dihydrochloride | 0.627 g |
| Oleic alcohol polyglycerolated to 2 moles glycerol | 4 g |
| Oleic alcohol polyglycerolated to 4 moles glycerol | 5.7 g |
| Oleic acid | 3 g |
| Oleic amine oxyethylenated to 2 moles ethylene oxide sold under the trade name ETHOMEEN 012 by AKZO | 7 g |
| Sodium salt of diethylaminopropyl laurylamino succinamate | 3 g |
| Oleic alcohol | 5 g |
| Oleic acid diethanolamide | 12 g |
| Propylene glycol | 3.5 g |
| Ethyl alcohol | 7 g |
| Dipropylene glycol | 0.5 g |
| Propylene glycol monomethyl ether | 9 g |

| | |
|---|---|
| Sodium metabisulfite, 35% aqueous solution | 0.45 g MA |
| Ammonium acetate | 0.8 g |
| Antioxidant, sequestrum producer qs | |
| Perfume, preservative qs | |
| Monoethanolamine pH: 9.8 qs | |
| Demineralized water qsp | 100 g |

The above composition was mixed just before use with an equal weight of 20 vol hydrogen peroxide whose pH had been adjusted to between 1 and 1.5 by addition of orthophosphoric acid (2.5 g orthophosphoric acid per 100 g of 20 vol hydrogen peroxide).

The pH of the mixture was equal to 6.5. The mixture was applied to gray hair with 90% white and left for 30 minutes at room temperature. The hair was rinsed, shampooed, rinsed again then dried. It had been dyed a light blue ash blond.

We claim:

1. A sulfated metaaminophenol coupler having the formula

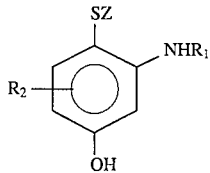

wherein

Z represents $C_1$–$C_{18}$ alkyl, aralkyl wherein the alkyl moiety has 1–6 carbon atoms, $C_1$–$C_6$ monohydroxyalkyl, $C_2$–$C_6$ polyhydroxyalkyl, aryl, aminoalkyl having the formula

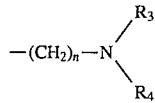

wherein n is a whole number ranging from 1 to 6 inclusive, $R_3$ and $R_4$, each independently, represent hydrogen, $C_1$–$C_4$ alkyl, $C_1$–$C_4$ hydroxyalkyl or $C_1$–$C_6$ acyl;

$R_1$ represents hydrogen, $C_1$–$C_6$ alkyl, $C_1$–$C_6$ hydroxyalkyl, $C_2$–$C_6$ polyhydroxyalkyl, $C_1$–$C_6$ monocarbamylalkyl, $C_1$–$C_6$ dicarbamylalkyl, $C_1$–$C_6$ aminoalkyl, ($C_1$–$C_6$) acylamino($C_1$–$C_4$)alkyl, carb($C_2$–$C_6$)alkoxy ($C_1$–$C_4$)alkyl, carbamyl or mono($C_1$–$C_6$)alkyl carbamyl;

$R_2$ represents hydrogen, $C_1$–$C_4$ alkyl, $C_1$–$C_4$ monohydroxyalkyl, or a $C_1$–$C_4$ alkoxy, or an acid addition salt thereof.

2. The sulfated metaaminophenol of claim 1 wherein Z represents methyl, ethyl, propyl, butyl, dodecyl, hexadecyl, benzyl, phenyl, —CH$_2$—CH$_2$—OH, —CH$_2$—CHOH—CH$_2$—OH, -CH$_2$—CHOH—CH$_3$, —CH$_2$—CH$_2$—NH$_2$, —CH$_2$—CH$_2$—NHCH$_3$, —CH$_2$—CH$_2$—NH—COCH$_3$, or

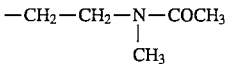

and $R_2$ represents hydrogen or $C_1$–$C_4$ alkoxy.

3. The sulfated metaaminophenol of claim 1 wherein said acid addition salt is a hydrochloride, a sulfate or a hydrobromide.

4. The sulfated metaaminophenol of claim 1 selected from the group consisting of 2-methoxy-4-methylthio-5-aminophenol and 4-methylthio-3-aminophenol.

* * * * *